(12) United States Patent
Chang et al.

(10) Patent No.: US 11,334,066 B2
(45) Date of Patent: May 17, 2022

(54) SAFETY MONITORING APPARATUS AND METHOD THEREOF FOR HUMAN-DRIVEN VEHICLE

(71) Applicant: PIXART IMAGING INC., Hsin-Chu (TW)

(72) Inventors: Yen-Min Chang, Hsin-Chu (TW); Chih-Yuan Chuang, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 0 days.

(21) Appl. No.: 15/972,385

(22) Filed: May 7, 2018

(65) Prior Publication Data

US 2018/0253094 A1    Sep. 6, 2018

Related U.S. Application Data

(63) Continuation-in-part of application No. 14/225,672, filed on Mar. 26, 2014, now abandoned.

(30) Foreign Application Priority Data

Mar. 27, 2013  (TW) .................................. 102110970

(51) Int. Cl.
   *G05D 1/00*    (2006.01)
   *G06T 7/90*    (2017.01)
   (Continued)

(52) U.S. Cl.
   CPC ........... *G05D 1/0061* (2013.01); *A61B 5/024* (2013.01); *A61B 5/02416* (2013.01);
   (Continued)

(58) Field of Classification Search
   CPC ........ G08G 1/166; G08G 1/167; B60Q 9/008; G08B 21/06; A61B 5/18; B60W 50/14;
   (Continued)

(56) References Cited

U.S. PATENT DOCUMENTS

2003/0086588 A1* 5/2003 Shinada .................. B60R 25/04
382/104
2007/0294746 A1* 12/2007 Sasakura ............. B60R 25/2018
726/2

(Continued)

*Primary Examiner* — Farhan Mahmud
(74) *Attorney, Agent, or Firm* — Li & Cai Intellectual Property (USA) Office (57) ABSTRACT

A safety monitoring apparatus and method thereof for human-driven vehicle are provided. The safety monitoring apparatus includes a sensing unit, a processing unit, and a warning unit. The sensing unit and the warning unit are electrically connected to the processing unit, respectively. The sensing unit is arranged on a steering member of the human-driven vehicle and is used for sensing whether the steering member is in contact with a hand of a driver and generating a sensing signal accordingly. The processing unit determines whether the hand of the driver is placed on the steering member. The warning unit is used for generating a safety warning message. When the processing unit determines that the hand of the driver has not been placed on the steering member according to the sensing signal, the processing unit drives the warning unit to generate the safety warning message to warn the driver.

19 Claims, 8 Drawing Sheets

(51) Int. Cl.
  *B60W 50/12* (2012.01)
  *B60W 50/14* (2020.01)
  *A61B 5/024* (2006.01)
  *A61B 5/1171* (2016.01)
  *A61B 5/145* (2006.01)
  *A61B 5/18* (2006.01)
  *A61B 5/00* (2006.01)
  *G06V 20/59* (2022.01)
  *G06V 40/10* (2022.01)
  *G06V 40/16* (2022.01)
  *H04L 67/125* (2022.01)
  *A61B 5/117* (2016.01)
  *A61B 5/1455* (2006.01)

(52) U.S. Cl.
  CPC ........ *A61B 5/1176* (2013.01); *A61B 5/14542* (2013.01); *A61B 5/18* (2013.01); *A61B 5/6893* (2013.01); *B60W 50/12* (2013.01); *B60W 50/14* (2013.01); *G05D 1/0055* (2013.01); *G06T 7/90* (2017.01); *G06V 20/597* (2022.01); *G06V 40/10* (2022.01); *G06V 40/172* (2022.01); *A61B 5/02405* (2013.01); *A61B 5/117* (2013.01); *A61B 5/14551* (2013.01); *B60W 2050/143* (2013.01); *B60W 2422/00* (2013.01); *B60W 2540/26* (2013.01); *G05D 2201/0213* (2013.01); *G06T 2207/30048* (2013.01); *G06T 2207/30268* (2013.01); *G06V 40/117* (2022.01); *G06V 40/15* (2022.01); *H04L 67/125* (2013.01)

(58) Field of Classification Search
  CPC ........ B60W 2540/22; B60W 2550/402; B60K 28/066; B60K 28/06; G01S 13/931; B60R 1/00; B62D 15/029
  See application file for complete search history.

(56) References Cited

U.S. PATENT DOCUMENTS

| | | | | |
|---|---|---|---|---|
| 2009/0209829 | A1* | 8/2009 | Yanagidaira | A61B 5/165 600/301 |
| 2010/0249628 | A1* | 9/2010 | Kortelainen | A61B 5/1102 600/527 |
| 2012/0101690 | A1* | 4/2012 | Srinivasan | G07C 9/00563 701/45 |
| 2014/0104405 | A1* | 4/2014 | Weidl | A61B 5/02416 348/77 |

* cited by examiner

SAFETY MONITORING APPARATUS AND METHOD THEREOF FOR HUMAN-DRIVEN VEHICLE

CROSS-REFERENCE TO RELATED PATENT APPLICATION

This U.S. Non-provisional application for patent is a continuation-in-part application of patent application Ser. No. 14/225,672 filed on Mar. 26, 2014. The entirety of each of the above-mentioned patent applications is hereby incorporated by reference herein and made as a part of this specification.

BACKGROUND

1. Technical Field

The present disclosure relates to a monitoring apparatus and a monitoring method thereof, in particular, to a safety monitoring apparatus and a method for a human-driven vehicle.

2. Description of Related Art

As technology advances, mobile vehicles, such as cars, buses, motorcycles, or bicycles, can provide door to door transportation convenience and comfort. e.g., people can be quickly and comfortably transported to a specific destination. Hence mobile vehicles have gradually become the dominant means of transportation in the modern life due to its convenience. However, when a mobile vehicle is driven by a driver with improper driving behaviors or dozes off while driving, or having discomfort, a traffic accident such as collision often results which usually causes injuries or even death to driver and/or passengers. For example, when a driver dozes off or under heart attack while on the road, a car accident may occur.

Recent years, a biological detector is installed in the mobile vehicle to detect the body temperature, the blood pressure, the pulse, and the blood glucose of the driver so as to prevent a mobile vehicle from causing an accident due to discomfort of a driver. For example, sensing electrodes for measuring the heartbeat or blood pressure are to be disposed on the body of the driver to monitor the biological state of the driver, and when detects that the biological state of the driver is abnormal, warn the driver instantly or notify a remote monitoring center for corresponding rescue operations.

SUMMARY

Accordingly, exemplary embodiments of the present disclosure provide a safety monitoring apparatus and a method thereof for a human-driven vehicle, which can effectively and instantly determine the driving safety of the human-driven vehicle through actively detecting whether a hand of a driver is placed on a steering apparatus of the human-driven vehicle.

An exemplary embodiment of the present disclosure provides a safety monitoring apparatus for a human-driven vehicle which includes a sensing unit, a processing unit, and a warning unit. The sensing unit is arranged on a steering member of the human-driven vehicle. The sensing unit is configured for sensing whether the steering member is in contacted with a hand of the driver and generating a sensing signal accordingly. The processing unit is electrically connected to the sensing unit. The processing unit operatively determines whether the hand of a driver is placed on the steering member according to the sensing signal. The warning unit is electrically connected to the processing unit and is configured for generating a safety warning message. When the processing unit determines that the hand of the driver has not been placed on the steering member according to the sensing signal, the processing unit outputs a warning signal causing the warning unit to generate a safety warning message to warn the driver.

An exemplary embodiment of the present disclosure further provides a safety monitoring method for a human-driven vehicle. The method includes the following steps. Whether a hand of a driver has been placed on the steering member is first detected with a sensing unit disposed on the steering member of the human-driven vehicle. When detects that the hand of the driver has not been placed on the steering member, generate a safety warning message to warn the driver.

To sum up, the exemplary embodiments of the present disclosure provide a safety monitoring apparatus and a method thereof for a human-driven vehicle which can through disposing sensors (e.g., touch sensors or switching components) on a steering member of the human driven vehicle (e.g., car or motorcycle,) actively determine whether the hand of a driver has been placed on the steering member while the driver drives the human-driven vehicle thereby reduce the possibility of traffic accident.

In order to further understand the techniques, means and effects of the present disclosure, the following detailed descriptions and appended drawings are hereby referred, such that, through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Reference will now be made in detail to the exemplary embodiments of the present disclosure, examples of which are illustrated in the accompanying drawings. Wherever possible, the same reference numbers are used in the drawings and the description to refer to the same or like parts.

[An Exemplary Embodiment of a Safety Monitoring System]

Figure 1:
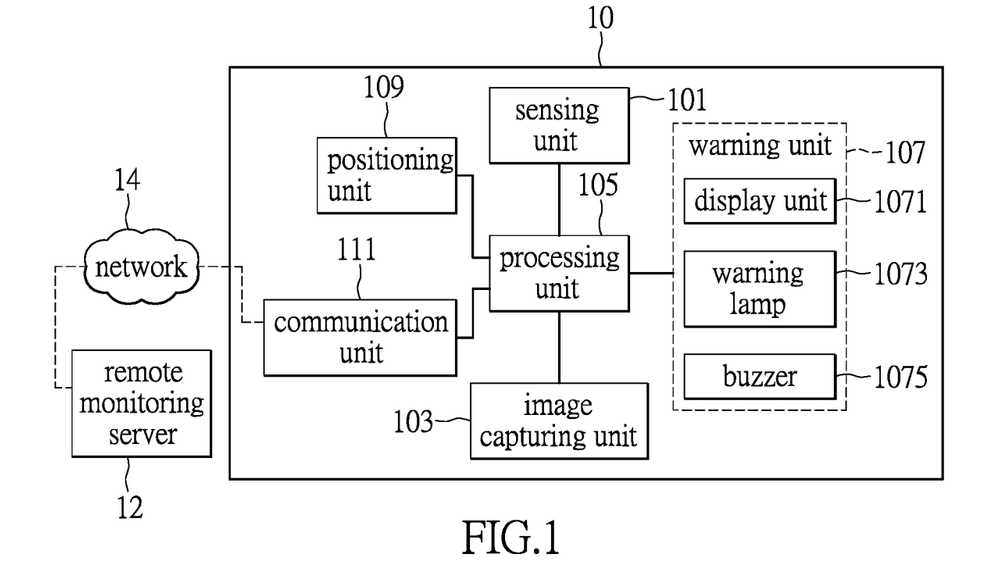
FIG. 1 is a functional block diagram of a safety monitoring system provided in accordance to an exemplary embodiment of the present disclosure.

Please refer to FIG. 1, which shows a functional block diagram of a safety monitoring system provided in accordance to an exemplary embodiment of the present disclosure. The safety monitoring system includes a safety monitoring apparatus 10 and a remote monitoring server 12. The safety monitoring apparatus 10 may connect to the remote monitoring server 12 through a network 14. The safety monitoring apparatus 10 can be used in a human-driven vehicle (e.g., a car, a bus, a motorcycle, and a bicycle), and can be integrated and disposed in the human-driven vehicle. The remote monitoring sever 12 can be configured and installed in a remote monitoring center (such as an ambulance center) for monitoring a driving safety of the human-driven vehicle through the network 14.

The safety monitoring apparatus 10 can be configured to detect whether a hand of a driver is placed on a steering member of the human-driven vehicle. That is, the safety monitoring apparatus 10 can detect whether the hand of the driver is placed the steering member. Those skilled in the art should understand that the phrase of "placed on the steering member" or "gripped on the steering member" have the same meaning throughout the entire context of the instant disclosure and are used interchangeably. The steering member may be, for example, a steering wheel of a car, or a handle of a motorcycle or a bicycle. The safety monitoring apparatus 10 can instantly generate a warning message to warn the driver when detects that the hand of the driver has not been placed on the steering member of the human-driven vehicle.

In short, the safety monitoring apparatus 10 may determine whether the driver is properly driving the human-driven vehicle at the instant through detect whether the hand of the driver has been placed on the steering member so as to monitor the driving safety of the human-driven vehicle. The safety monitoring apparatus 10 can also notify an operator of the remote monitoring server 12 to analyze the driving safety of the human-driven vehicle and the biological state of the driver when continually detects that the hand of the driver has not placed on the steering member of the human-driven vehicle.

Specifically, the safety monitoring apparatus 10 includes a sensing unit 101, an image capturing unit 103, a processing unit 105, a warning unit 107, a positioning unit 109, and a communication unit 111. The sensing unit 101, the image capturing unit 103, the warning unit 107, the positioning unit 109, and the communication unit 111 are electrically connected to the processing unit 105 respectively.

The sensing unit 101 is arranged on the steering member of the human-driven vehicle. The sensing unit 101 is configured to sense whether the hand of the driver has been placed on the steering member and generate a sensing signal based on the sensing result. The sensing unit 101 may be implemented by one of a tact switch and a touch switch, or a combination thereof so as to sense whether the hand of the driver is presently placed on the steering member.

In one embodiment, the sensing unit 101 may be a tact switch, and the tact switch can be disposed on the steering member. Accordingly, the sensing unit 101 may sense whether the hand of the driver is placed on the steering member by sensing whether the driver presses the steering member. In another embodiment of the present disclosure, the sensing unit 101 may be a touch switch, and the touch switch can be disposed on the steering member. Such that the sensing unit 101 may sense whether the hand of the driver is placed on the steering member through touch sensing. In addition, the sensing unit 101 may be implemented by a touch sensor including but not limited to a capacitive touch sensor, a resistive touch sensor, an optical touch sensor, and an ultrasonic sensor.

It should be noted that, since the hand of the driver may not be necessary placed on the position of the steering member corresponding to the sensor unit 101, hence it is preferable that the sensing unit 101 comprises more than one tact switch or touch switch positioned at an equal distance or an equal angle on the steering member so as to accurately and effectively sense whether the steering member has been touched by the driver.

Particularly, the sense unit 101 may selectively output a sensing signal of a high voltage level or a low voltage level to the processing unit 105 based on the sensing result of the steering member for the processing unit 105 to determine whether or not the steering member is been touched. Taking the sensing unit 101 as a tact switch for example, when the sensing unit 101 determines that the hand of the driver has been placed on the steering member (i.e., the tact switch on the steering member is pressed or triggered), the sensing unit 101 may output a sensing signal with high voltage level to the processing unit 105. Conversely, when the sensing unit 101 determines that the hand of the driver has not been placed on the steering member (i.e., the tact switch on the steering member has not been pressed), the sensing unit 101 may output a sensing signal with low voltage level to the processing unit 105. Accordingly, the processing unit 105 may determine whether the hand of the driver has been placed on the steering member according to the voltage level of the sensing signal outputted by the sensing unit 101.

The image capturing unit 103 is configured for capturing a facial image of the driver of the human-driven vehicle, and correspondingly outputs at least an image data to the processing unit 105. The image capturing unit 103 may also correspondingly calibrate optimal image capturing parameters to properly capture the facial image of the driver based on the condition of surrounding environment and generate the image data. The image capturing unit 103 may be installed in the human-driven vehicle facing the direction of the driver seat.

Taking the human-driven vehicle as a car for an example, the image capturing unit 103 may be installed on the dashboard or the windshield in front of the driver seat, however, the present embodiment is not limited herein. The image capturing unit 103 may be an image capturing device including but not limited to a web camera or a PC video camera, or a video recorder, however the present disclosure is not limited to the examples listed herein.

The processing unit 105 can determine whether the steering member is in contact with the hand of a driver according to the sensing signal. In other words, the processing unit 105 can determine whether the hand of the driver has been placed on the steering member according to the sensing signal. The warning unit 107 is configured for generating a safety warning message to warn the driver to place the hand on the steering member. Moreover, the processing unit 105 can drive the warning unit 107 to continuously warn the driver until the sensing unit 101 outputs the sensing signal indicating that the hand of the driver has been placed on the steering member. The warning unit 107 further includes a display unit 1071, a warning lamp 1073, and a buzzer 1075.

Briefly, when the processing unit 105 determines that the hand of the driver has not been placed on the steering member according to the sensing signal, the processing unit 105 immediately outputs a warning signal to drive the warning unit 107 to generate the safety warning message to warn the driver. Specifically, the processing unit 105 can operatively control the display unit 1071 of the warning unit 107 to display a safety warning message, such as, "Please place your hand on the steering member". The processing unit 105 may also operatively control the warning lamp 1073 of the warning unit 107, e.g., turn on or flashing a lamp to warn the driver. The processing unit 105 can also at the same time control the buzzer 1075 to generate a warning sound effect to warn the driver. For instance, whenever the driver dozes off while driving the human-driven vehicle and unconsciously releases the steering member, the buzzing sound of the buzzer 1075 can quickly wake up the driver and normally drives the human-driven vehicle. The processing unit 105 may subsequently output a clear signal to the warning unit 107 so as to stop generating the safety warning message when the sensing signal received indicates that either the hand of the driver has been placed on the steering member or the driver grips on the steering member.

It is worth to mention that the processing unit 105 can also output the warning signal to operatively control the warning unit 107 generating the safety warning message to warn the driver after the sensing unit 101 senses that the hand of the driver has not been placed on the steering member for a predetermined time (e.g., 2 seconds). The processing unit 105 can also regularly (e.g., every 5 seconds) control the sensing unit 101 to sense whether the hand of the driver is in contact with the steering member of the human-driven vehicle so as to constantly monitor the safety of the human-driven vehicle.

Next, the processing unit 105 may obtain a heart rate data corresponding to the change in the heart rate of the driver and determine the biological state of the driver through analyzing the image data being corresponding to the facial image of the driver. More specifically, the processing unit 105 may operatively drive the image capturing unit 103 to capture the facial image of the driver regularly. The processing unit 105 may further apply image processing to the image data and analyze the brightness information of at least a color (e.g., three primary colors including red, green or blue) in the image data to generate the heart rate data corresponding to the change in the heart rate of the driver.

The image processing methods described herein may include color-based segmentation, gray scale conversion, image filtering, image binarization, edge extraction, feature extraction, image compression, and image segmentation. In practice, those skilled in the art may program the processing unit 105 to select and apply appropriate image processing techniques according to the image recognition requirements.

The image processing method may include gray scale transformation, image filtering, image binarization, edge detection, feature extraction, image compression, and image segmentation. In practice one may select an appropriate image processing technique to be the image processing method for the processing unit 203 to use according to the image recognition requirement.

Moreover, the processing unit 105 can determine whether the heart rate of the driver obtained falls within a predetermined range. When the processing unit 105 determines that the heart rate of the driver exceeds the predetermined range, the processing unit 105 operatively drive the warning unit 107 to generate a biological state warning message, e.g., causing the display unit 1071 of the warning unit 107 to display a message indicating abnormal heart rate so as to advice the driver to stop driving the human-driven vehicle as soon as possible. The predetermined range may for instance be a normal heart rate range, or a normal heart rate range established based on the biological state of the driver.

It is worth to note that those skilled in the art should know that the heart rate curve of each person is periodic and unique, thus, the processing unit 105 can identify or recognize the identity of the driver by analyzing the heart rate data. To put it concretely, the processing unit 105 can compare a heart rate data of the driver obtained with a predetermined heart rate data to identify the identity of the driver. The predetermined heart rate data may a heart rate data of the owner of the human-driven vehicle prerecorded or preconfigured in the processing unit 105.

When the processing unit 105 determines that the heart rate data of the driver does not match the predetermined heart rate data indicating that, the present driver is not the owner of the human-driven vehicle, the processing unit 105 can operatively transmit a control signal to the human-driven vehicle to prohibit the present driver from driving the human-driven vehicle. Conversely, when the processing unit 105 determines that the heart rate data matches the predetermined heart rate data i.e., verify that the present driver is the owner of the human-driven vehicle, the processing unit 105 allows the present driver to start and drive the human-driven vehicle.

In short, before the driver start the human-driven vehicle, the processing unit 105 may actively drive the image capturing unit 103 to capture the image data corresponds to the facial image of the driver of the human-driven vehicle so as to obtain the heart rate data associated with the driver of the human-driven vehicle. The processing unit 105 may thus identify the identity of the present driver through analyzing the heart rate data of the driver obtained. The processing unit 105 further determines whether to allow the driver to start the human-driven vehicle based on the analysis result.

Accordingly, the disclosed safety monitoring apparatus 10 not only capable of determining the driving safety of the human-driven vehicle but also capable of identify the identity of the driver of the human-driven vehicle. The human-driven vehicle can thus effectively prevent the human-driven from being used unauthorizedly or stolen thereby increases the anti-theft security of the human-driven vehicle.

Incidentally, the processing unit 101 can through perform image processing analysis and feature extraction operations on the image data and determine whether the driver sits in a correct driving position. When the processing unit 105 determines that the driver sits in incorrect driving position e.g., in the co-driver seat or in the passenger seats, the processing unit 105 may also output the control signal to the human-driven vehicle to prohibit the driver from driving the human-driven vehicle.

The safety monitoring apparatus 10 further includes a positioning unit 109 and a communication unit 111. The positioning unit 109 is configured for generating a positioning signal corresponding to a present position of the human-driven vehicle, wherein the positioning signal may be, for example, the latitude and the longitude data of the human-driven vehicle. The positioning unit 109 can locate the human-driven vehicle using a Global Positioning Satellite device or a wireless base station. The communication unit 111 may be connected to a remote monitoring server 12 through a network 14 to transmit the sensing signal, the heart rate data, and the positioning signal to the remote monitoring server 12, wherein the network 14 may be a wired network or a wireless network. The communication unit 111 may also connect to a portable electronic device with communication capability, e.g., a mobile phone, a personal digital assistant (PDA), or a tablet, such that the driver can communicate with a monitoring center through the portable electronic device in case of emergency, for example, the driver can use the mobile phone call the remote monitoring center for help or related assistance.

When the processing unit 105 determines that the hand of the driver has not been placed on the steering member (i.e., the steering member has not been touched) for the predetermined time according to the sensing signal received, the processing unit 105 may operatively drive the communication unit 111 to transmit the sensing signal and the positioning signal to the remote monitoring center 12, so that the operator at the remote monitoring center 12 can instantly monitor the human-driven vehicle, or provide immediate rescue service.

For instance, when the processing unit 105 determines that the hand of the driver has not been placed on the steering member for the predetermined time according to the sensing signal indicating that something might happen to the driver while driving the human-driven vehicle e.g., the driver is dozing off or is in discomfort, the processing unit 105 may immediately transmit the sensing signal and the positioning signal to the remote monitoring server 12 through the communication unit 111. When the processing unit 105 determines that the heart rate data of the driver exceeds the predetermined range, that is, the biological state of the driver is abnormal, the processing unit 105 may also transmit the heart rate data and the positioning signal to the remote monitoring sever 12 so that the operator of the remote monitoring server 12 can send emergency medical personnel for corresponding rescue operations. The safety monitoring apparatus 10 can thus help reduce the occurrence of accidents and improve the driving safety of the human-driven vehicle.

It is worth to note that the predetermined range, the predetermined heart rate data, as well as the heart rate data generated by the processing unit 105 based on the image data may be stored in a storage unit (not shown) of the safety monitoring apparatus 10. The storage unit in the embodiment may be implemented by a volatile memory chip or a nonvolatile memory chip such as a flash memory chip, a read-only memory chip, or a random access memory chip, however the instant embodiment is not limited thereto. The processing unit 105 may be implemented by a processing chip such as a central processing unit (CPU), a microcontroller, or an embedded controller disposed in the safety monitoring apparatus 10, however the instant embodiment is not limited to the example provided herein.

In the instant embodiment, the image capturing unit 103 is integrated in the safety monitoring apparatus 10, however, in practice the image capturing unit 103 can be externally connected to the safety monitoring apparatus 10 in a wireless manner or a wire manner. The image capturing unit 103 may be connected to the safety monitoring apparatus 10 through transmission interface including but not limited to universal serial bus (USB), Recommended Standard 232 (RS-232), PS/2, Bluetooth, wireless internet interface, or Ethernet so as to transmit the image data corresponding to the facial image of the driver to the safety monitoring apparatus 10. The transmission interface of the image capturing unit 103 described herein is merely serve as an example to illustrate feasible connection methods between the image capturing unit 103 and the safety monitoring apparatus 10, and the instant embodiment is not limited thereto.

It should be noted that FIG. 1 is merely used for illustrating a functional block diagram for a safety monitoring system, and the present disclosure is not limited thereto. The type, actual structure, implementation method, and/or connection method associated with the sensing unit 101, the image capturing unit 103, the processing unit 105, the warning unit 107, the positioning unit 109, and the communication unit 111 depend on the actual implementation of the safety monitoring apparatus 10, and the instant embodiment is not limited thereto.

[Another Exemplary Embodiment of a Safety Monitoring Apparatus]

Besides detecting whether the hand of the driver is placed on the steering member, the safety monitoring apparatus can also at the same time detect the biological information of the driver and enable the driver to monitor his/her own biological state. Please refer to FIG. 2, which shows a functional block diagram of a safety monitoring apparatus provided in accordance to an exemplary embodiment of the present disclosure.

Figure 2:
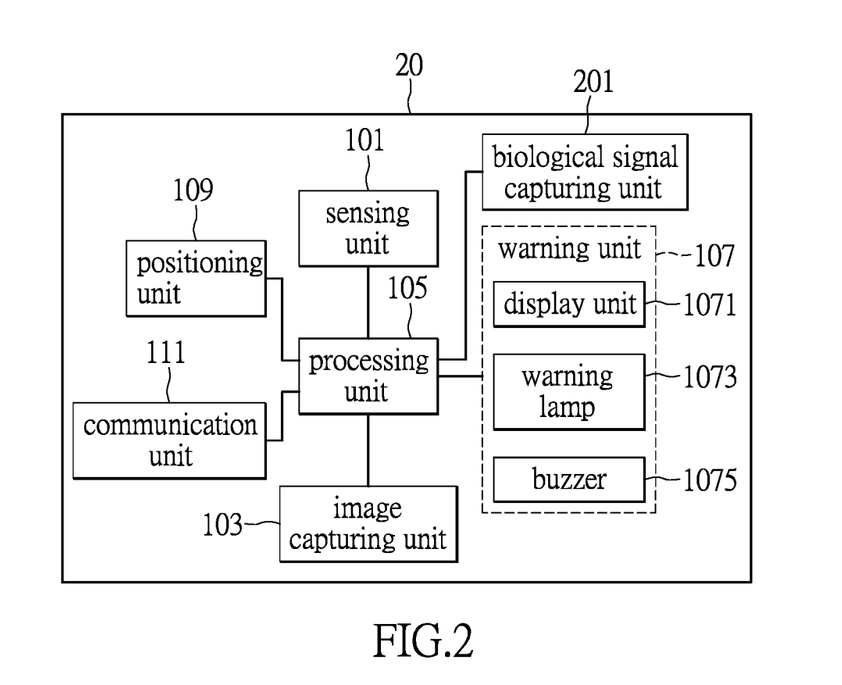
FIG. 2 is a functional block diagram of a safety monitoring apparatus provided in accordance to an exemplary embodiment of the present disclosure.

The safety monitoring apparatus 20 is disposed in the human-driven vehicle and is configured for determining whether the hand of the driver is placed on the steering member of the human-driven vehicle while driving the human-driven vehicle. When the safety monitoring apparatus 20 determines that the steering member is not in contact with the hand of the driver, the safety monitoring apparatus 20 generates a warning message to warn the driver. The safety monitoring apparatus 20 may further connect to a remote monitoring server (not shown) located in a remote monitoring center (such as a Medicare ambulance service center) through a network (not shown) using the communication unit 111 so that the personnel (e.g., an operator) at the remote monitoring center can instantly and remotely monitor the driving safety of the human-driven vehicle.

The difference between the safety monitoring apparatus 20 in FIG. 2 and the safety monitoring apparatus 10 in FIG. 1 is that the safety monitoring apparatus 20 further includes a biological signal capturing unit 201. The biological signal capturing unit 201 is electrical connected to the processing unit 105 of the safety monitoring apparatus 20. In the instant embodiment, the biological signal capturing unit 201 is disposed on the steering member and is configured for sensing at least one biological signal corresponding to the biological characteristic of the driver so that the processing unit 105 can analyze the biological state of the driver. That is, the safety monitoring apparatus 20 not only can monitor the heart rate curve of the driver by analyzing the image data corresponding to the facial image of the driver, but also can monitor the change in the biological state of the driver using the biological signal capturing unit 201.

In the instant embodiment, the biological signal capturing unit 201 can be a Photoplethysmogram (PPG), such that the signal outputted by the biological signal capturing unit 201 is a PPG signal. The PPG can optically measure the blood volume changes in the peripheral vessels (e.g., arterioles) with each cardiac beat.

The blood flow in a vessel changes periodically with each cardiac beat, the PPG thus can detect the blood volume changes through measuring the amount of light absorption of blood vessels. That is, the PPG can utilize light sensing element to sense the blood volume changes and generate the PPG signal, correspondingly, hence the amplitude of the PPG signal is proportional to the change in blood flow in the human body. At the same time, the period of the PPG signal is also corresponding to the period of each cardiac beat.

More specifically, the biological signal capturing unit 201 may include a light emitter (not shown), such as an infrared light emitting diode or a red light emitting diode, and a light sensing component (not shown), such as a photodiode or a phototransistor. The light emitter and the light sensing component can be respectively disposed on the steering member. In one embodiment, the light emitter and the light sensing component may be disposed on the steering member with the sensing unit 201, respectively. The light sensing component may further be configured to sense whether the hand of the driver has been placed on the steering member.

In the exemplary embodiment, the biological signal capturing unit 201 is a reflective PPG, such that the light emitter and the light sensing component can be correspondingly disposed on the same side, e.g., both disposed on the top side or on the bottom side of the steering member, wherein the spacing between the light emitter and the light sensing component may be configured depend upon the width of the palm of the hand e.g., less than 1 centimeter (cm). In practice, those skilled in the art may also design the spacing between the light emitter and the light sensing component based on their actual need so long as the light sensing component is able to sense the light emitted by the light emitter to measure the blood volume change in the peripheral vessels of the driver. Accordingly, when the hand of the driver grips on the steering member, the biological signal capturing unit 201 can sense the blood volume change in the peripheral vessels in the body of the driver as the hand of the driver presses or touches the light emitter and the light sensing component.

The processing unit 105 can then analyze the heart rate variability (HRV) of the driver (i.e., the person under test) according to the PPG signal outputted by the biological signal capturing unit 201. Please refer to FIG. 3, which shows a diagram illustrating a typical PPG signal provided in accordance an exemplary embodiment of the present disclosure. Curve C10 represents a waveform of the PPG signal, wherein the PPG signal as previously described is a periodical signal which corresponds to the cardiac beat. As depicted by curve C10, the first half cycle in each cycle corresponds to the waveform measured when the heart contracts, while the second half cycle in each cycle corresponds to the waveform measured when the heart relaxes. The processing unit 105 can perform computation to the curve C10 to obtain the number of the heartbeat as well as the variability of heart rate.

Figure 3:
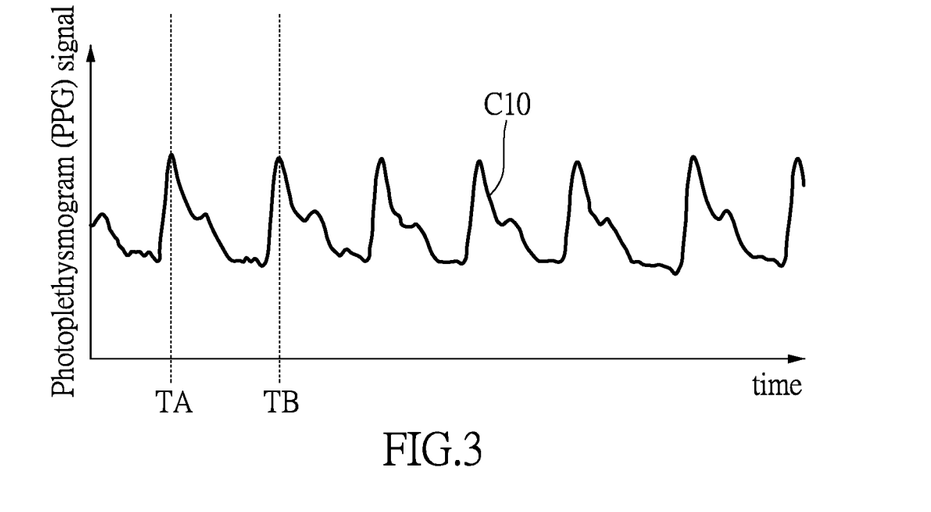
FIG. 3 is a diagram illustrating a typical PPG signal provided in accordance to an exemplary embodiment of the present disclosure.

As shown in FIG. 3, the maximal peak value of the curve C10 of each cycle occurs when the heart contracts, thus the processing unit 105 can through counting the number of the maximal peak value (e.g., the time point TA and TB) occurred within a period of time (e.g., every minute) to obtain the number of cardiac beats of the driver during the period of time. The peak to peak interval of the curve C10, e.g., the interval from the time point TA to the time point TB, represents the beat to beat interval. The processing unit 105 may thus generate the heart rate variability of the driver from computing the peak to peak interval of curve C10 so as to analyze the biological state of the driver.

Besides, the processing unit 105 can further calculate the peak to peak interval of each cycle from curve C10 to obtain interval variation of each cardiac beat. The processing unit 105 can subsequently to analyze state of the nervous system of the driver via computation of the power spectral density (PSD). For example, the low frequency component of the power spectrum can be used as the index of vagal modulation of the sympathicus and the parasympathetic while the high frequency component of the power spectrum can be used to acquire the state of the parasympathetic nervous system. The technique for analyzing the heart rate variability of the driver and the state of the sympathicus are known in the field, and those skilled in the art should be able to infer the analysis of the PPG signal and the related algorithm, hence further descriptions are hereby omitted. Accordingly, the processing unit 105 can effectively and accurately analyze the biological state of the driver with the biological signal capturing unit 201.

Incidentally, the processing unit 105 can also transmit the biological signal sensed by the biological signal capturing unit 201 to the remote monitoring server to perform related data processing and analysis, such that the operator of the remote monitoring server can directly analyze the biological state of the driver. Hence, the computational resource requirement of the safety monitoring device 20 can be reduced while accelerating the analyzation of the biological signal and the conversion of the biological data.

In practice, the biological signal capturing unit 201 may also include a plurality of light sources for emitting light into the skin tissue of the driver and receive the light reflected/emitted from the skin tissue with the optical sensor. Such that, the blood oxygen level can be calculated according to the light absorption level of the vessels responsive to different wavelengths of light, for instance, the blood oxygen level may be computed according to the ratio of light energy level sensed by the optical sensor to the energy level initially emitted for different wavelengths of light. On the other hand, the biological information e.g., pulse, may also be derived according to the light absorption variation for a single light wavelength.

One important aspect of the present disclosure is on the noise processing method to obtain a better signal. More specifically, receive lights with different wavelength simultaneously and compare the light rays based on the time or the power distribution. Or, drive the light source to emit a wide range of lights and filters with various filters disposed on the optical sensor to correspondingly obtain frequency responses for the lights with different wavelength. Such that the pressure index such as heart rate variability can be further derived after simultaneously obtains the biological information including the image data, the PPG signal, fingerprints, and the heart beat signal.

The present disclosure may further dispose an array of sensing units responsive to different wavelengths of light so as to have different region covered by the respective sensing unit receiving the transmissive/reflective signals of different wavelength. So that two sets of lights (e.g., wavelengths of 660 nm and 940 nm) can be simultaneously emitted and senses by different sensing units. Currently, the measurement of the blood oxygen level uses a single light sensing unit accompany with time division multiplexing technique to measure two signals of different wavelengths. Particularly, a light of 660 nm and a light of 940 nm are emitted separately i.e., one at time. Hence, the reflectivity of a human tissue in responsive to two different sets of light sources cannot be analyzed at same time.

In another embodiments, the placement of the biological signal capturing unit 201 may be arranged corresponding to the positions of the hand and the foot, so that the biological signal (e.g., the PPG signal) can be measured from different body positions. Accordingly, biological signals sensed from different body positions can be analyzed so as to conduct a risk evaluation analysis for possible occurrence of vascular occlusion. The risk evaluation analysis can be used for a health reminder to air traveler. Moreover, for a computer mouse user, the biological signal capturing unit 201 can be disposed on a grip position or on a button position. Such that the data related to the fatigue level of the user can be generated through accumulating the biological signal for a predetermined time and perform analysis correspondingly. If the computer mouse user has become too tire due to continuously operating the mouse for a long time or for several days, the computer mouse can operatively warn the computer mouse user to rest via changing the operation of the computer mouse such as flicking the cursor or modifying the pattern of the cursor, or causing the computer mouse to stop outputting coordinate information for the cursor, or disable the computer mouse so as to encourage the computer mouse user to take rest for a while or take another PPG signal measurement.

In practice, the biological signal capturing unit 201 may further includes a biological detecting device, which is configured for measuring the body temperature, the blood pressure, the blood sugar level, the breath, brainwave or eye-ball movement. The biological signal capturing unit 201 can be disposed on any other positions that can be used to monitor the driver of the human-driven vehicle according to actual architecture and application, and the instant embodiment is not limited thereto. The biological signal capturing unit 201 may be externally connected to the safety monitoring apparatus 20 and may transmit the biological signal detected to the processing unit 105 of the safety monitoring apparatus 20 in a wired or a wirelessly or manner for the processing unit 105 to perform the related biological analysis. Or, the safety monitoring apparatus 20 may also directly transmit the biological signal received from the biological signal capturing unit 201 to a remote monitoring server through a network using the communication unit 111 for the operator of the remote monitoring server to determine and analyze the biological state of the driver and to instantly monitor the health as well as the driving safety of the driver.

The rest of the structures of the safety monitoring apparatus 20 are essentially the same as those of the safety monitoring apparatus 10 and based on the above elaborations, those skilled in the art should be able to infer the operation associated with the safety monitoring apparatus 20, hence further descriptions are therefore omitted.

[Application Embodiment of the Safety Monitoring Apparatus]

Figure 4A:
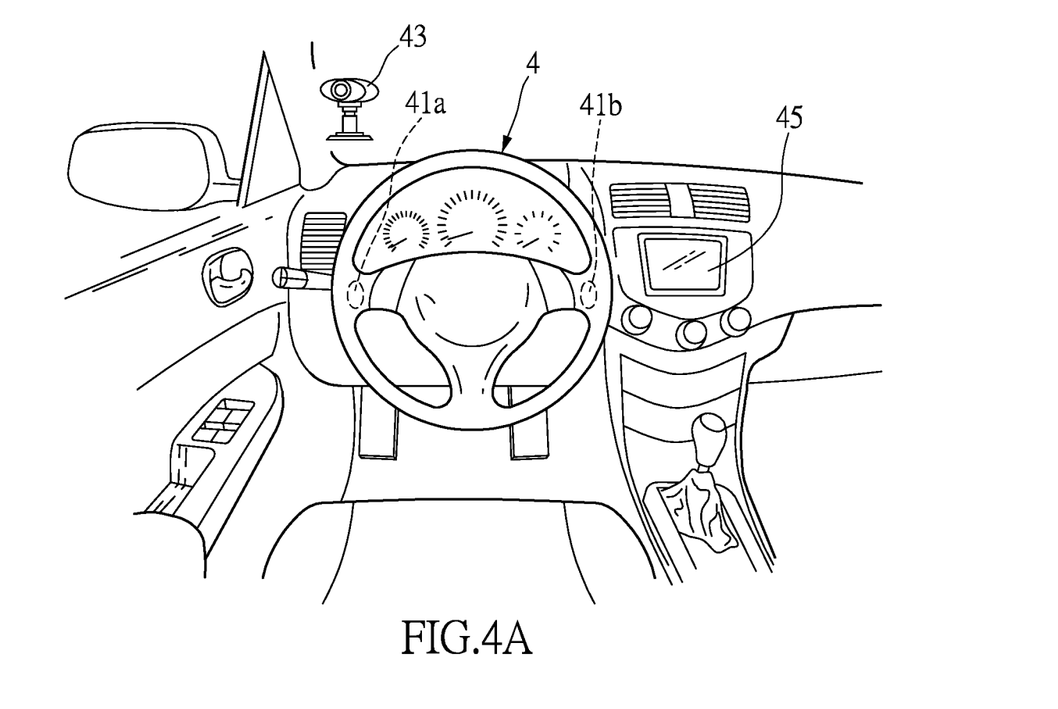
FIG. 4A is a schematic diagram illustrating an application of a safety monitoring apparatus in a human-driven vehicle provided in accordance to an exemplary embodiment of the present disclosure.
Figure 4B:
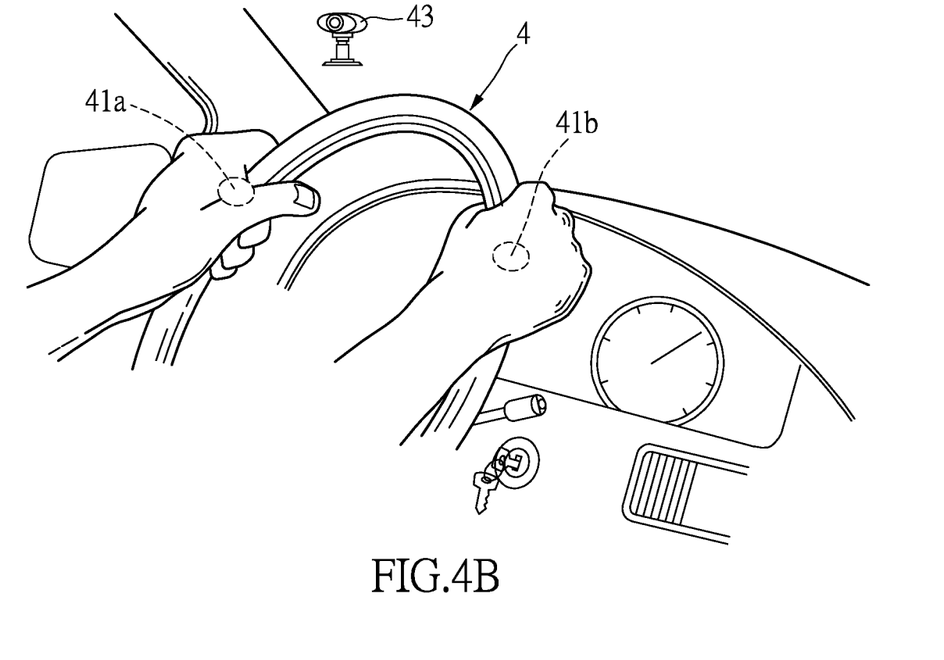
FIG. 4B is a schematic diagram illustrating a user-gripping operation of a steering member provided in accordance to an exemplary embodiment of the present disclosure.

Please refer to FIG. 4A and FIG. 4B. FIG. 4A shows a schematic diagram illustrating an application a safety monitoring apparatus in a human-driven vehicle provided in accordance to an exemplary embodiment of the present disclosure to a human-driven vehicle. FIG. 4B shows a schematic diagram illustrating a user-gripping operation of a steering member provided in accordance to an exemplary embodiment of the present disclosure.

In the instant embodiment, a car is taken as the human-driven vehicle, and the safety monitoring apparatus may be installed inside the car. Specifically, the sensing unit of the safety monitoring apparatus in the instant embodiment includes two touch switches 41a, 41b, and the touch switches 41a, 41b are respectively disposed on the steering wheel 4 of the car for sensing whether the hand of the driver has been placed on the steering wheel 4. An image capturing unit 43 (e.g., a webcam) is installed or mounted on the windscreen of the car while faces the driver for capturing the facial image of the driver.

In short, before the car starts, the processing unit (not shown in FIG. 4A and FIG. 4B) of the safety monitoring apparatus operatively obtain the heart rate data of the driver for identifying the identity of the driver according to the image data related to the facial image of the driver captured by the image capturing unit 43. When the identity of the driver is determined to be invalid, the processing unit of the safety monitoring apparatus can transmit a control signal to the starting system of the car to prohibit the driver from driving the car. While the driver drives the car, the processing unit operatively controls the touch switches 41a, 41b to sense whether the hand of the driver has been placed on the steering wheel 4.

When the touch switches 41a, 41b simultaneously sense or senses that the hand of the driver has not been placed on the steering wheel 4 after a period of time, the processing unit operatively control the warning unit (e.g., cause a display unit 45 to display a safety warning message to warn the driver, activate a buzzer to generate a warning sound, or a turn on a warning lamp). When the touch switches 41a, 41b sense that the hand of the driver has been placed on or has gripped on the steering wheel 4 (as shown in FIG. 4B), the processing unit may stop the operation of the warning unit (e.g., clear the safety warning message displayed on the display unit 45, de-active the operation of the buzzer, or turn on the warning lamp).

When the processing unit of the safety monitoring apparatus continuously determines that the hand of the driver has not placed on the steering wheel 4 according to the sensing signal sensed by the touch switches 41a, 41b, the processing unit transmits the sensing signal and the positioning signal to a remote monitoring server (not shown in FIG. 4A and FIG. 4B) to notify the operator of the remote monitoring server to take a corresponding measure, such as communicate with the driver or send emergency medical personnel to the site to verify the condition of the driver.

The processing unit may constantly control the image capturing unit 43 to capture the facial image of the driver regularly while the driver drive the human-driven vehicle to analyze the heart rate of the driver according to the image data outputted by the image capturing unit 43 so that the driver can instantly monitor his/her own biological state.

Thus, the safety monitoring apparatus can reduce the probability of traffic accident occurred as the result of improper driving behavior or the driver being unable to drive normally due to discomfort.

Figure 5:
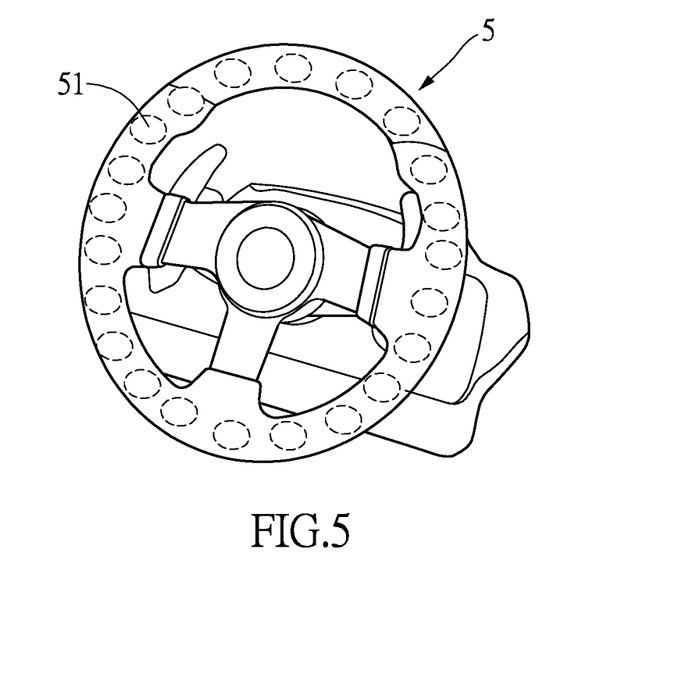
FIG. 5 is a schematic diagram illustrating an arrangement of the sensing unit provided in accordance to an exemplary embodiment of the present disclosure.

As described previously, the sensing unit can also include a plurality of touch switches to accurately sense whether the hand of the driver is placed on or grips the steering wheel 4. Please refer to FIG. 5 which shows a schematic diagram illustrating an arrangement of the sensing unit provided in accordance to an exemplary embodiment of the present disclosure. As shown in FIG. 5, the sensing unit includes a plurality of touch switches 51 configured to sense the driver for gripping the steering wheel 5 at different angle or in different manners. The touch switches 51 may be arranged on the steering wheel 5 at an equal distance. In other embodiment, the touch switches 51 may also be respectively arranged on the steering wheel 5 at an equal angle. The aforementioned biological signal capturing unit may also be disposed on the steering wheel 5 along with the sensing unit such that, the heart rate variability can be simultaneously detected while sensing whether the hand of the driver has been placed on the steering wheel 5.

It is worth to note that the instant embodiment uses a touch switch to illustrate the operation of the sensing unit, however, the sensing unit may also be implemented by one of a tact switch, a capacitive touch sensor, a resistive touch sensor, an optical touch sensor, and an ultrasonic sensor. The actual architecture and arrangement of the sensing unit may be configured according to an actual application requirement. In other words, FIG. 4A and FIG. 4B are merely used to show a diagram illustrating applying a safety monitoring apparatus onto a car and the present disclosure is not limited thereto. FIG. 5 is merely used to show a schematic diagram illustrating an arrangement of disposing the sensing unit on the steering wheel 5 and the present disclosure is not limited thereto.

[An Exemplary Embodiment of a Safety Monitoring Method]

Figure 6:
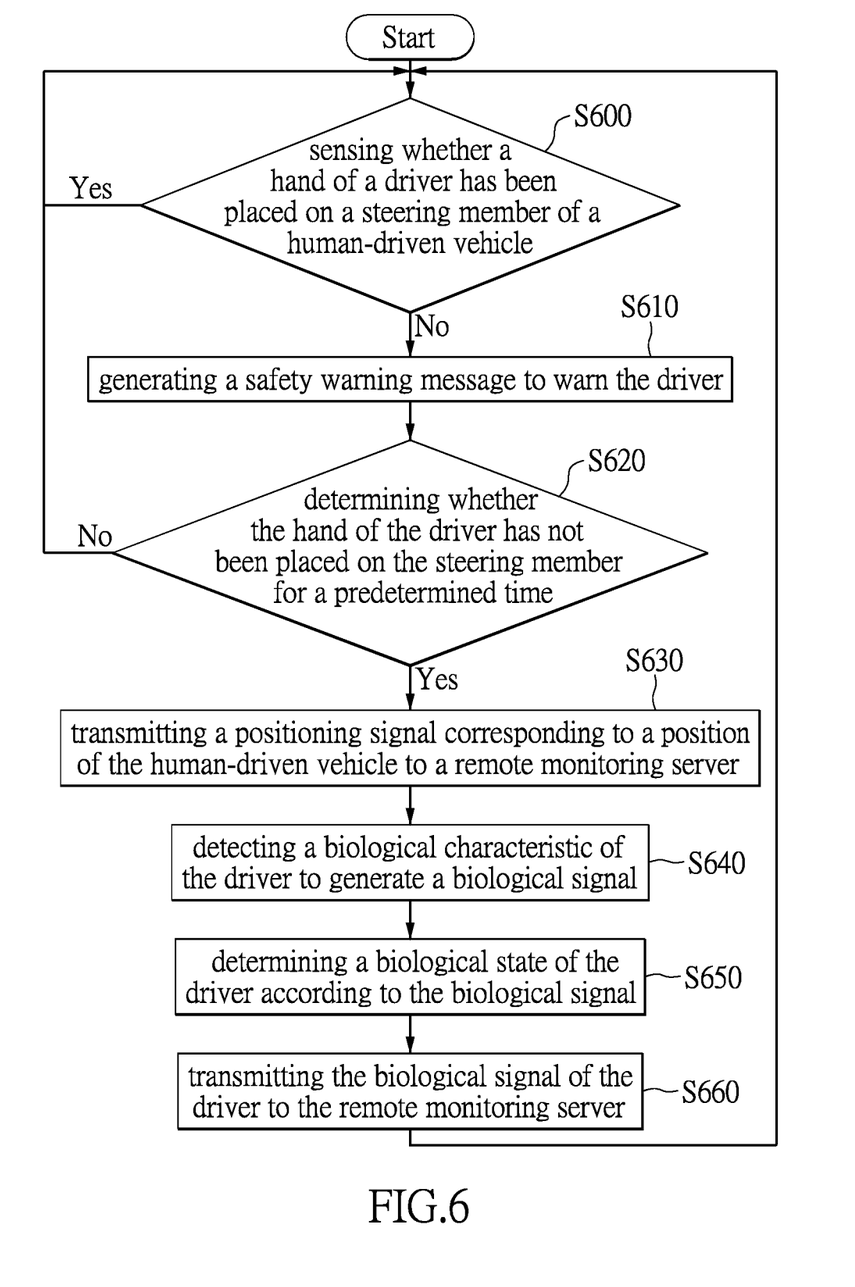
FIG. 6 is a flowchart illustrating a safety monitoring method for a human-driven vehicle provided in accordance to an exemplary embodiment of the present disclosure.

From the aforementioned exemplary embodiments, the present disclosure may generalize a safety monitoring method for a human-driven vehicle, such as a traffic vehicle such as a car, a bus, a motorcycle, a bicycle and etc., and the safety monitoring method can be adapted for the safety monitoring apparatus described in the aforementioned exemplary embodiments. Please refer to FIG. 6 in conjunction with FIG. 1, wherein FIG. 6 shows a flowchart illustrating a safety monitoring method for a human-driven vehicle provided in accordance to an exemplary embodiment of the present disclosure.

In Step S600, the processing unit 105 determines whether a hand of a driver is presently in contact with the steering member of the human-driven vehicle is sensed. More specifically, the processing unit 105 can operatively drive the sensing unit 101 being disposed on the steering member of the human-driven vehicle to sense whether the hand of the driver has been placed on the steering member of the human-driven vehicle.

When the processing unit 105 determines that the hand of the driver has not being in contact with the steering member of the human-driven vehicle according to the sensing signal generated by the sensing unit 101, executes Step S610. Conversely, when the processing unit 105 determines that the hand of the driver is presently in contact with the steering member of the human-driven vehicle according to the sensing signal, returns to Step S600.

In Step S610, the processing unit 105 of the safety monitoring apparatus 10 generates a safety warning message to warn the driver. The processing unit 105 can operatively control a display unit 1071 of a warning unit 107 to display the safety warning message, control the warning lamp 1073 to turn on or flicker, control the buzzer 1075 to generate a warning sound effect, or a combination thereof to warn the driver to drive the human-driven vehicle normally.

In Step S620, the processing unit 105 further determines whether the hand of the driver still has not been in contact with the steering member for a predetermined time. When the processing unit 105 determines that the hand of the driver still has not been in contact with the steering member according to the sensing signal for the predetermined time, executes Step S630. Conversely, when the processing unit 105 determines that the hand of the driver has been in contact with the steering member according to the sensing signal, returns to Sep S600.

In step S630, the processing unit 105 transmits a positioning signal and a sensing signal corresponding to the human-driven vehicle to a remote monitoring server. The processing unit 105 can drive the positioning unit 109 to generate a positioning signal corresponding to the human-driven vehicle. The positioning signal can be the latitude and the longitude data of the human-driven vehicle. The processing unit 105 further transmits the positioning signal and a sensing signal corresponding to the position of the human-driven vehicle through a network to a remote monitoring server using a communication unit 111.

Next, in Step S640, the biological characteristic of the driver is detected to generate at least one biological signal. The biological signal may include at least one of a heart rate signal, a pulse signals and a blood-oxygen signal. For example, the processing unit 105 may operatively drive the image capturing unit or the biological signal capturing unit 201 in FIG. 2 to detect and capture the biological characteristic such as the heart rate, the pulse or blood-oxygen level of a driver in a contact or noncontact manner so as to generate a biological signal, correspondingly.

In Step S650, the processing unit 105 can determine the biological state of the driver according to the biological signal. When the processing unit 105 determines that the biological state of the driver is abnormal according to the biological signal, such as the heart rate of the driver exceeds a predetermined range, the blood oxygen level is lower than a standard blood oxygen level (e.g., lower than 90%), or the body temperature of the driver is lower than a predetermined temperature, the processing unit 105 operatively drive the warning unit 107 to correspondingly generate a biological state warning message to warn the driver.

In Step S660, a biological state describing the biological characteristic of the driver is transmitted to a remote monitoring server so that an operator of the remote monitoring server can analyze the instant biological state of the driver. The operator of the remote monitoring server can further determine whether it is necessary to conduct a rescue operation to rescue the driver o according to the biological signal so that in case of emergency the driver can be rescued or helped immediately when the biological state of the driver become abnormal. Accordingly, the occurrence probability of accident can be reduced while the driving safety of the human-driven vehicle can be enhanced.

Figure 7:
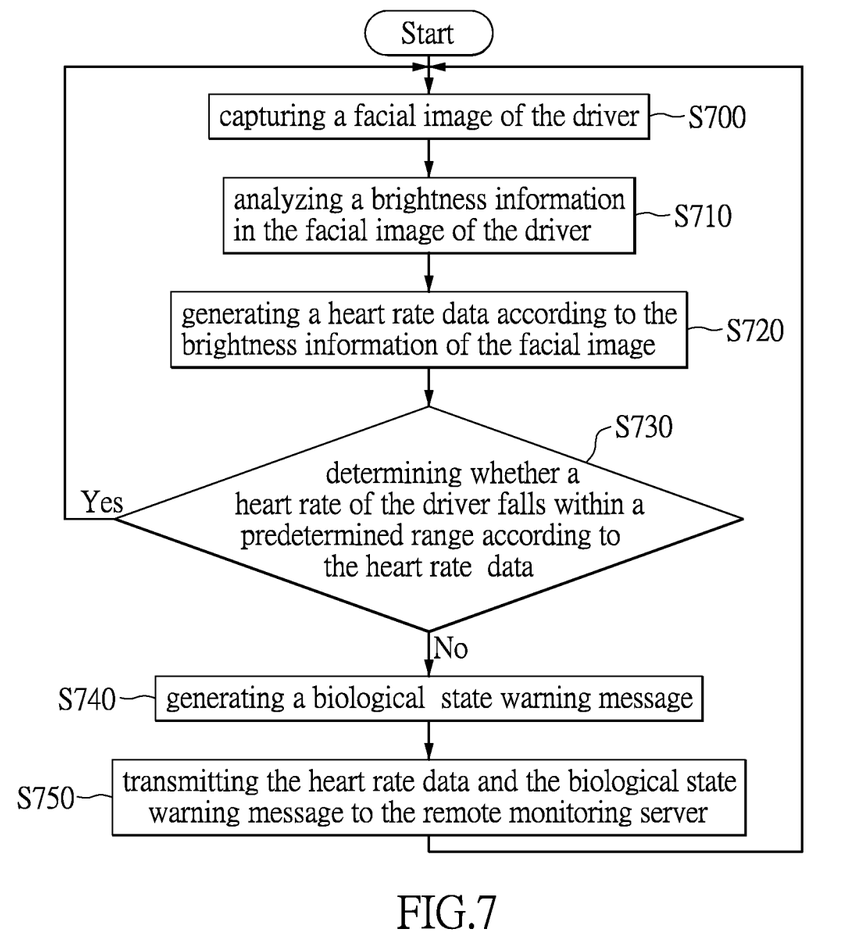
FIG. 7 is a flowchart illustrating a method for detecting and analyzing biological characteristics of a driver provided in accordance to an exemplary embodiment of the present disclosure.

The present disclosure further provides a method of using an image capturing unit to detect the biological characteristic of a driver in a non-invasive or noncontact manner. Please refer to FIG. 7 in conjunction with FIG. 1, wherein FIG. 7 shows a flowchart illustrating a method for detecting and analyzing the biological characteristics of a driver provided in accordance to an exemplary embodiment of the present disclosure.

In Step S700, the processing unit 105 drives the image capturing unit 103 to capture the facial image of the driver to generate at least an image data. In Step S710, the processing unit 105 analyzes the brightness information of at least one color in the image data based on the image data. In other words, the processing unit 105 can analyze the brightness information of each primary color (e.g., red, green, blue) in the image data with image processing techniques. In Step S720, the processing unit 105 can generate correspondingly a heart rate data of the driver from analyzing the brightness information of each primary color in the image data.

In Step S730, the processing unit 105 determines whether the heart rate of the driver falls within the predetermined range according to the heart rate data. The predetermined range of the heart rate may be, for example, a normal heart rate range or a normal heart rate range established based on the biological state of the driver. When the processing unit 105 determines that the heart rate of the driver exceeds the predetermined range according to the heart rate data, executes Step S740. Conversely, when the processing unit 105 determines that the heart rate of the driver has not exceed the predetermined range according to the heart rate data, returns to Step S700.

In Step S740, the processing unit 105 operatively drives the warning unit 107 to correspondingly generate a biological state warning message. For example, the processing unit 105 operatively controls the display unit 1071 to display a heart rate abnormal message to notify the driver to stop driving the human-driven vehicle as soon as possible.

In step S750, the processing unit 105 can transmit the heart rate data and the biological state warning message to the remote monitoring server using the communication unit 111.

Additionally, the processing unit 105 can also control a biological signal capturing unit (not shown in FIG. 1) including but not limited to, a PPG an electrocardiography, a thermometer, and a glucosemeter, to detect the biological characteristics of the driver so as to generate a heart rate signal, a pulse rate signal, a temperature signal, and a blood-oxygen signal to inform the driver on his/her biological state.

Incidentally, when the processing unit 105 programmed to use the biological signal capturing unit 201 in FIG. 2 to perform Step S640 in FIG. 6 to detect the biological characteristic of the driver e.g., the heart rate, the pulse, and the blood-oxygen level, the processing unit 105 can also simultaneously programmed to execute the biological characteristic capturing method of FIG. 7 using the image capturing unit 103 to obtain the heart rate data of the driver via image analysis. The processing unit 105 further analyzes and compares the biological characteristic detection results of the biological signal capturing unit 201 and the image capturing unit 103 to accurately analyze the biological state of the driver.

Figure 8:
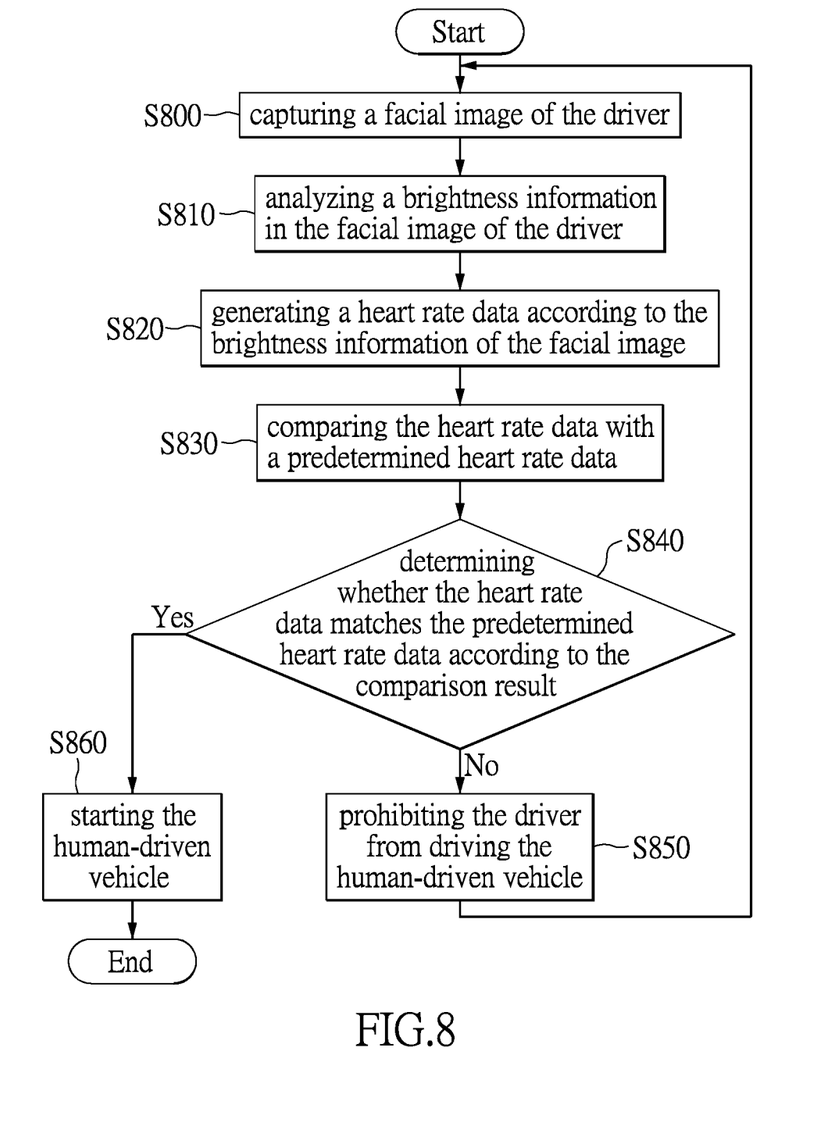
FIG. 8 is a flowchart illustrating a method for identifying the identity of a driver provided in accordance to an exemplary embodiment of the present disclosure.

The present disclosure further provides a method for identifying the identity of a driver based on the heart rate determined. Please refer to FIG. 8 in conjunction with FIG. 1, wherein FIG. 8 shows a flowchart illustrating a method for identifying the identity of a driver provided in accordance to an exemplary an embodiment of the present disclosure. The method for identifying the identity of a driver in FIG. 8 can be performed before the driver starts the human-driven vehicle so as to determine whether to allow the present driver to drive the human-driven vehicle.

In Step S800, the processing unit 105 drives the image capturing unit 103 to capture the facial image of the driver so as to generate at least an image data. In Step S810, the processing unit 105 analyzes the brightness information of at least one color in the image data based on the image data. Then, in Step S820, the processing unit 105 correspondingly generates the heart rate data of the driver by analyzing the brightness information of each primary color in the image data.

Next, in Step S830, the processing unit 105 compares the heart rate data instantly obtained with a predetermined heart rate data. The predetermined heart rate data may be the heart rate data of the owner of the human-driven vehicle pre-recorded in the processing unit 105. In Step S840, the processing unit 105 determines whether the heart rate data of the driver obtained matches the predetermined heart rate data based on the comparison result. When the processing unit 105 determines that the heart rate data of the driver does not match the predetermined heart rate data (i.e., the present driver is not the owner of the human-driven vehicle), executes Step S850. Conversely, when the processing unit 105 determines that the heart rate data of the driver matches the predetermined heart rate data (i.e., the present driver is the owner of the human-driven vehicle), executes Step S860.

In Step S850, the processing unit 105 transmits a control signal to the human-driven vehicle to prohibit the driver from driving the human-driven vehicle. In Step S860, the processing unit 105 allows the driver to start and drive the human-driven vehicle.

Incidentally, the processing unit 105 may also determines whether the driver presently sits in a correct driving position (i.e., the driver seat) based on analyze at lease an image data from the image capturing unit 103. When the processing unit 105 determines that the driver does not sit in the correct driving position, the processing unit 105 transmits a control signal i to the human-driven vehicle to prohibit the driver from driving the human-driven vehicle.

When the biological signal capturing unit (not shown in FIG. 1) operates under ambient light, the interference generated by the ambient light needs to be taken into consideration. In practice, a typical ambient light interference is the flickering frequency of a lamp. Though the naked eyes cannot notice the flickering of a lamp tube due to the effect of visual persistence, however, the ambient light interference can still interfere with the sensing operation of the biological signal capturing unit.

For instance, when a light emitter (not shown in FIG. 1) and the optical sensor (not shown in FIG. 1) of the biological signal capturing unit are disposed in an open space, the optical sensor is very sensitive to the change of an ambient light. The present disclosure provides a possible solution to tackle the described interference issue, i.e., subtracting signal in-phase. Specifically, taking a 360 degrees cycle as an example, subtracts in-phase signals in two adjacent cycles to cancel the interference, wherein no light is emitted in one cycle so that only the ambient light is detected in that particular cycle, such that the flickering noise generated by the ambient light can be eliminated. Please refer to FIG. 9, which shows a diagram illustrating a waveform of a light sensing signal sensed by an optical sensor provided in accordance to an exemplary embodiment of the present disclosure. The light source herein is implemented by an LED light source. In the Nth cycle and the N+1th cycle, the LED light source emits light while in N+2th cycle and the N+3th cycle, no light is emitted from the LED light source. Thus, the flickering noise generated by the ambient light can be eliminated by subtracting the light sensing signal of the N+2th cycle from the light sensing signal of the Nth cycle. Similarly, the flickering noise generated by the ambient light can be also be eliminated by subtracting the light sensing signal of the N+3th cycle from the light sensing signal of the N+1th cycle.

Figure 9:
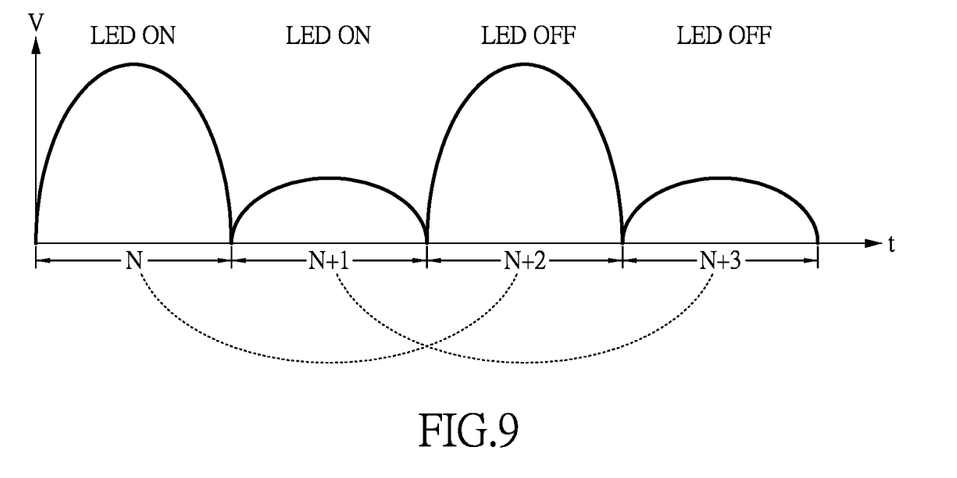
FIG. 9 is a diagram illustrating a waveform of a light sensing signal sensed by an optical sensor provided in accordance to an exemplary embodiment of the present disclosure.

The safety monitoring method illustrated in FIG. 6, the biological characteristic detecting method illustrated in FIG. 7, and the method for identifying the identity of a driver illustrated in FIG. 8 can be implemented by writing the corresponding firmware into the processing unit 105 of the safety monitoring apparatus 10. The processing unit 105 can be implemented by a processing chip such as a central processing unit (CPU), a microcontroller, or an embedded controller, disposed in the safety monitoring apparatus 10, however the instant embodiment is not limited thereto. The safety monitoring method illustrated in FIG. 6, the biological characteristic detecting method illustrated in FIG. 7 and the method for identifying the identity of a driver illustrated in FIG. 8 are merely used to explain the operations of the safety monitoring apparatus, and the present disclosure is not limited thereto. FIG. 9 merely shows a schematic diagram for illustrating a sensed light sensing signal sensed by an optical sensor during an operation of the biological signal capturing unit, and the present disclosure is not limited thereto.

Moreover, the biological signal capturing unit can also be used to identify an identity of a driver, e.g., analyzes the veins distribution of a driver from an image captured. After identified the identity of the driver, the biological signal capturing unit can also configure the safety monitoring apparatus to operate in a personalized setting according to the biological state of the driver and the identity of different drivers.

Figure 10:
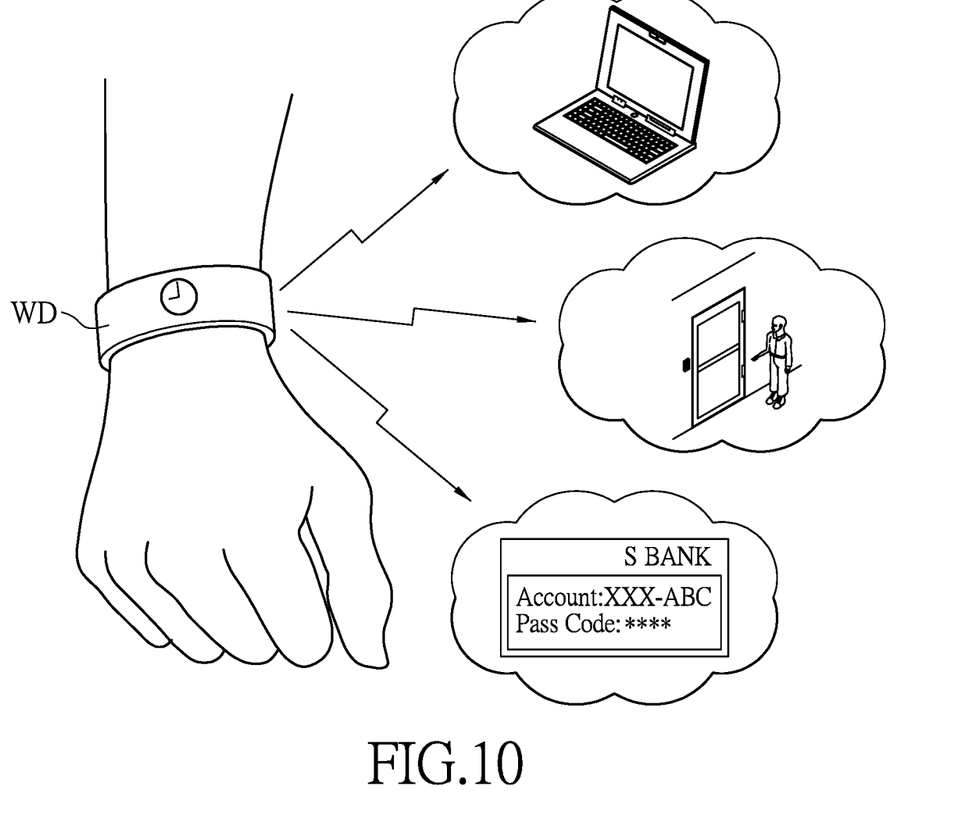
FIG. 10 shows a schematic diagram for illustrating a situation where the biological signal capturing unit is used to identify the identity of a driver.

FIG. 10 shows a schematic diagram for illustrating a situation where the biological signal capturing unit is used to identify the identity of a driver. In this embodiment, the safety monitoring apparatus can work with a wearable device WD that can detect biological features of the driver. In other words, there can be a signal transmission or a data transmission between the safety monitoring apparatus and the wearable device WD. For example, as shown in FIG. 10, the wearable device WD can be a smart watch. After the safety monitoring apparatus identifies the driver's identity, the safety monitoring apparatus transmits an identification signal to the wearable device WD. Once the wearable device WD receives the identification signal, it can be used as an unlock means, such as an electronic key or a registration tool. As long as the driver does not take off the wearable device WD, he can use the wearable device WD to unlock a door having an electronic lock, a computer or even a bank account. However, these examples are only for illustrating the application situations where the biological signal capturing unit of the safety monitoring apparatus is used to identify the identity of a driver, but not for restricting the present disclosure.

[Possible Efficacy of Embodiments]

In summary, the exemplary embodiments of the present disclosure provide a safety monitoring apparatus and a safety monitoring method for a human-driven vehicle, which can through disposing sensors actively determine whether a hand of a driver has been placed on the steering member of the human-driven vehicle while the driver drives the human-driven vehicle so as to instantly determine the vehicle safety of the human-driven vehicle thereby reduce the possibility of a traffic accident. Additionally, the present disclosure further provide a non-invasive biological characteristic detecting method which can obtain a heart rate curve of the driver from analyzing the brightness information from the facial image of the driver captured and quickly identify the identity of the driver based on the heart rate curve obtained thereby increase the anti-theft security of the human-driven vehicle.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A safety monitoring apparatus for a human-driven vehicle, comprising:
an image capturing unit, configured for capturing a facial image of a driver and correspondingly generating at least one image data for generating at least one heart rate data;
a biological signal capturing unit, configured to optically measure the driver to sense at least one biological signal of the driver; and
a processing unit, electronically connected to the image capturing unit, and obtaining the heart rate data of the driver so as to determine whether a heart rate of the driver falls within a predetermined heart rate data;
wherein the processing unit analyzes a brightness information of at least a color in the image data so as to obtain the heart rate data corresponding to the change in the heart rate of the driver;
wherein the processing unit compares the heart rate data with the predetermined heart rate data to identify the identity of the driver before the human-driven vehicle starts; when the processing unit determines that the heart rate data does not match the predetermined heart rate data, the processing unit operatively transmits a control signal to the human-driven vehicle to prohibit the driver from driving the human-driven vehicle;
wherein the biological signal capturing unit can also be used to identify the identity of the driver by analyzing a heart rate of the driver from the at least one image data;
wherein after the safety monitoring apparatus identifies the driver's identity, the safety monitoring apparatus transmits an identification signal to a wearable device, and once the wearable device receives the identification signal, the wearable device can be used as an unlock means without further identification as long as the wearable device is not taken off from the driver.

2. The safety monitoring apparatus according to claim 1, further comprising:
a warning unit, electronically connected to the processing unit, and configured for generating a safety warning message; and
a sensing unit, arranged on a steering member of the human-driven vehicle for sensing whether the steering member of the human-driven vehicle is in contact with a hand of a driver and generating a sensing signal, accordingly, wherein when the sensing unit causes the processing unit to output the warning signal after senses that the hand of the driver has not placed on the steering member for a predetermined time.

3. The safety monitoring apparatus according to claim 2, wherein the sensing unit comprises one of a tact switch and a touch switch.

4. The safety monitoring apparatus according to claim 2, wherein the sensing unit comprises one of a capacitive touch sensor, a resistive touch sensor, an optical touch sensor, and an ultrasonic sensor.

5. The safety monitoring apparatus according to claim 2, wherein when the processing unit determines that the heart rate of the driver exceeds the predetermined heart rate data, the processing unit drives the warning unit to generate a biological state warning message.

6. The safety monitoring apparatus according to claim 2, further comprising:

a positioning unit, electronically connected to the processing unit, and used for generating a positioning signal corresponding to a position of the human-driven vehicle; and a communication unit, electronically connected to the processing unit, and used for connecting to a remote monitoring server through a network to transmit the sensing signal and the positioning signal to the remote monitoring server.

7. The safety monitoring apparatus according to claim 6, wherein when the processing unit continuously determines that the hand of the driver has not been placed on the steering member according to the sensing signal for a period of time, the processing unit controls the communication unit to transmit the sensing signal and the positioning signal to the remote monitoring server.

8. The safety monitoring apparatus according to claim 1, wherein the image data is used for determining whether the driver sits in a correct driving position.

9. The safety monitoring apparatus according to claim 1, wherein the biological signal capturing unit is disposed on the steering member.

10. The safety monitoring apparatus according to claim 9, wherein the biological signal capturing unit is a Photoplethysmogram (PPG).

11. The safety monitoring apparatus according to claim 1, wherein the wearable device remains as the unlock means as long as the wearable device is worn properly.

12. A safety monitoring method for a human-driven vehicle, comprising:
    sensing whether a hand of a driver has been placed on a steering member using a sensing unit disposed on the steering member of the human-driven vehicle;
    generating a safety warning message through a warning unit to warn the driver when sensed that the hand of the driver has not been placed on the steering member according to a sensing signal generated by the sensing unit;
    analyzing a brightness information of at least a color in an image data to generate a heart rate data;
    comparing the heart rate data with a predetermined heart rate data to identify the identity of the driver by a processor; and
    transmitting a control signal to the human-driven vehicle to prohibit the driver from driving the human-driven vehicle when determining that the heart rate data does not match the predetermined heart rate data;
    wherein the identity of the driver can also be identified via a biological signal capturing unit by analyzing a heart rate of the driver from the at least one image data;
    wherein after the safety monitoring apparatus identifies the driver's identity, the safety monitoring apparatus transmits an identification signal to a wearable device, and once the wearable device receives the identification signal, the wearable device can be used as an unlock means without further identification as long as the wearable device is not taken off from the driver when the heart rate data matches the predetermined heart rate data.

13. The safety monitoring method according to claim 12, further comprising:
    driving the sensing unit to sense whether the driver still has not placed the hand on the steering member for a predetermined time after determines that the hand of the driver has not been placed on the steering member.

14. The safety monitoring method according to claim 12, wherein the step after generating the safety warning message to warn the driver comprises:
    detecting a biological characteristic of the driver to generate at least one biological signal; and
    determining a biological state of the driver according to the biological signal;
    wherein the biological signal comprises at least one of a heart rate signal, a pulse signal, and a blood oxygen signal.

15. The safety monitoring method according to claim 14, wherein the step of detecting the biological characteristic of the driver comprises:
    capturing a facial image of the driver to generate at least an image data.

16. The safety monitoring method according to claim 15, wherein the step after generating the heart rate data comprises:
    determining whether a heart rate of the driver falls within a predetermined range according to the heart rate data; and
    generating a biological state warning message when determines that the heart rate of the driver exceeds the predetermined range.

17. The safety monitoring method according to claim 12, wherein when the identity of the driver is identified, the safety monitoring apparatus transmits an identification signal to a wearable device such that the wearable device is used as an unlock means.

18. The safety monitoring method according to claim 12, wherein the step after generating the safety warning message to warn the driver comprises:
    transmitting a positioning signal corresponding to a position of the human-driven vehicle to a remote monitoring server through a network when continuously senses that the driver has not been placed the hand on the steering member for a period of time.

19. A safety monitoring method for a human-driven vehicle, comprising:
    sensing whether a hand of a driver has been placed on a steering member using a sensing unit disposed on the steering member of the human-driven vehicle;
    generating a safety warning message to warn the driver when sensed that the hand of the driver has not been placed on the steering member according to a sensing signal generated by the sensing unit;
    capturing a facial image of the driver to generate at least an image data;
    analyzing a brightness information of at least a color in the image data to generate a heart rate data;
    comparing the heart rate data with a predetermined heart rate data to identify the identity of the driver; and
    transmitting an identification signal from a safety monitoring apparatus to a wearable device such that the wearable device is used as an unlock means when the identity of the driver is identified as long as the wearable device is not taken off from the driver;
    wherein the identity of the driver can also be identified via a biological signal capturing unit by analyzing a heart rate of the driver from the at least one image data.

* * * * *